(12) United States Patent  
Hsiao (10) Patent No.: US 8,192,041 B2  
(45) Date of Patent: Jun. 5, 2012

(54) SAFE ILLUMINATING FRAGRANT DEVICE

(76) Inventor: Ming-Jen Hsiao, Miaoli County (TW)

( * ) Notice: Subject to any disclaimer, the term of this patent is extended or adjusted under 35 U.S.C. 154(b) by 249 days.

(21) Appl. No.: 12/614,446

(22) Filed: Nov. 9, 2009

(65) Prior Publication Data

US 2011/0110072 A1　May 12, 2011

(51) Int. Cl.  
*F21V 33/00* (2006.01)

(52) U.S. Cl. ............................ 362/96; 362/101; 362/643

(58) Field of Classification Search .................. 362/96, 362/101, 253, 254, 643, 234  
See application file for complete search history.

(56) References Cited

U.S. PATENT DOCUMENTS

| | | | | |
|---|---|---|---|---|
| 4,816,973 A * | 3/1989 | Atalla et al. | ................... | 362/643 |
| 6,478,440 B1 * | 11/2002 | Jaworski et al. | ................ | 362/96 |
| 7,357,561 B2 * | 4/2008 | Hidalgo et al. | ............... | 362/643 |
| 7,674,001 B1 * | 3/2010 | Ferrin et al. | ................... | 362/101 |
| 7,832,891 B2 * | 11/2010 | Zhou | ............................. | 362/192 |
| 7,840,123 B2 * | 11/2010 | Belongia et al. | .............. | 392/392 |

* cited by examiner

*Primary Examiner* — John A Ward (57) ABSTRACT

A safe illuminating fragrant device has a base, electric circuit, case body, and an electrothermal unit. The base has a through hole, and the electric circuit is arranged in the base. The electric circuit has a plurality of lighting components capable of emitting light in predetermined color. The case body covers the base. A plurality of apertures is arranged around a peripheral of the case body with a predetermined interval. Lights from the lighting components will go into the case body and project out through the apertures. A receiving slot is formed to a top of the case body for receiving spices, and the electrothermal unit will heat up a bottom of the receiving slot. A safety and visual effect are improved by above assembly.

10 Claims, 8 Drawing Sheets

SAFE ILLUMINATING FRAGRANT DEVICE

FIELD OF THE PRESENT INVENTION

The present invention relates fragrant device, and particular to a safe illuminating fragrant device capable of dissipating fragrance by heat and with illuminating feature.

DESCRIPTION OF THE PRIOR ART

The prior fragrant oven uses electric heater to heat up the oven. A burning accident is easily happened while essential oil leaking to the heater because the electrical heater is not insulated.

Another prior fragrant device using a lamp to heat up essential oil or wax also has problems of low efficiency of dissipating fragrance and concern of fire.

Above devices usually have complicated assembly so that it is hard to disassemble, move, and clean while needed. Also, it is not easy to switch spices applied to the device.

Moreover, the fragrant oven and devices using lamp can not provide illumination feature in the same time.

SUMMARY OF THE PRESENT INVENTION

Accordingly, the primary object of the present invention is to provide a safer fragrant device with lighting feature.

A secondary object of the present invention is to provide a safe illuminating fragrant device capable of dissipating fragrant fast.

Another object of the present invention is to provide a safe fragrant device with features of illumination and visual effect.

A yet object of the present invention is to provide a safe illuminating fragrant device which is easily to disassemble and assemble spice container for cleaning so that user can easily switch different spices such as essential oil, wax, or dried herb.

The material of the invention can be different styles of glass, ground glass, acrylic, crystal, or transparent ceramic.

DETAILED DESCRIPTION OF THE INVENTION

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
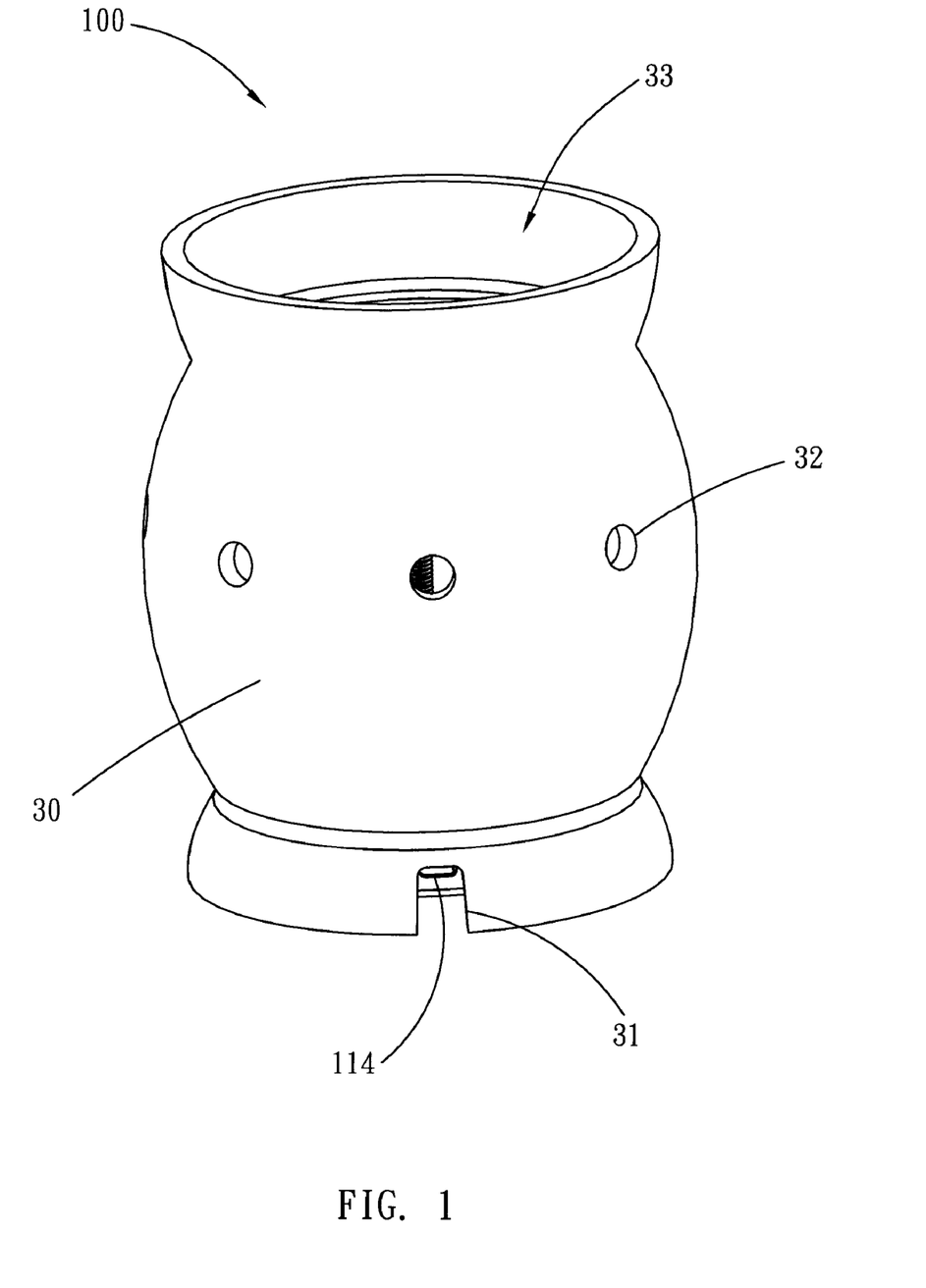
FIG. 1 is a schematic view showing a preferable embodiment of the present invention.
Figure 2:
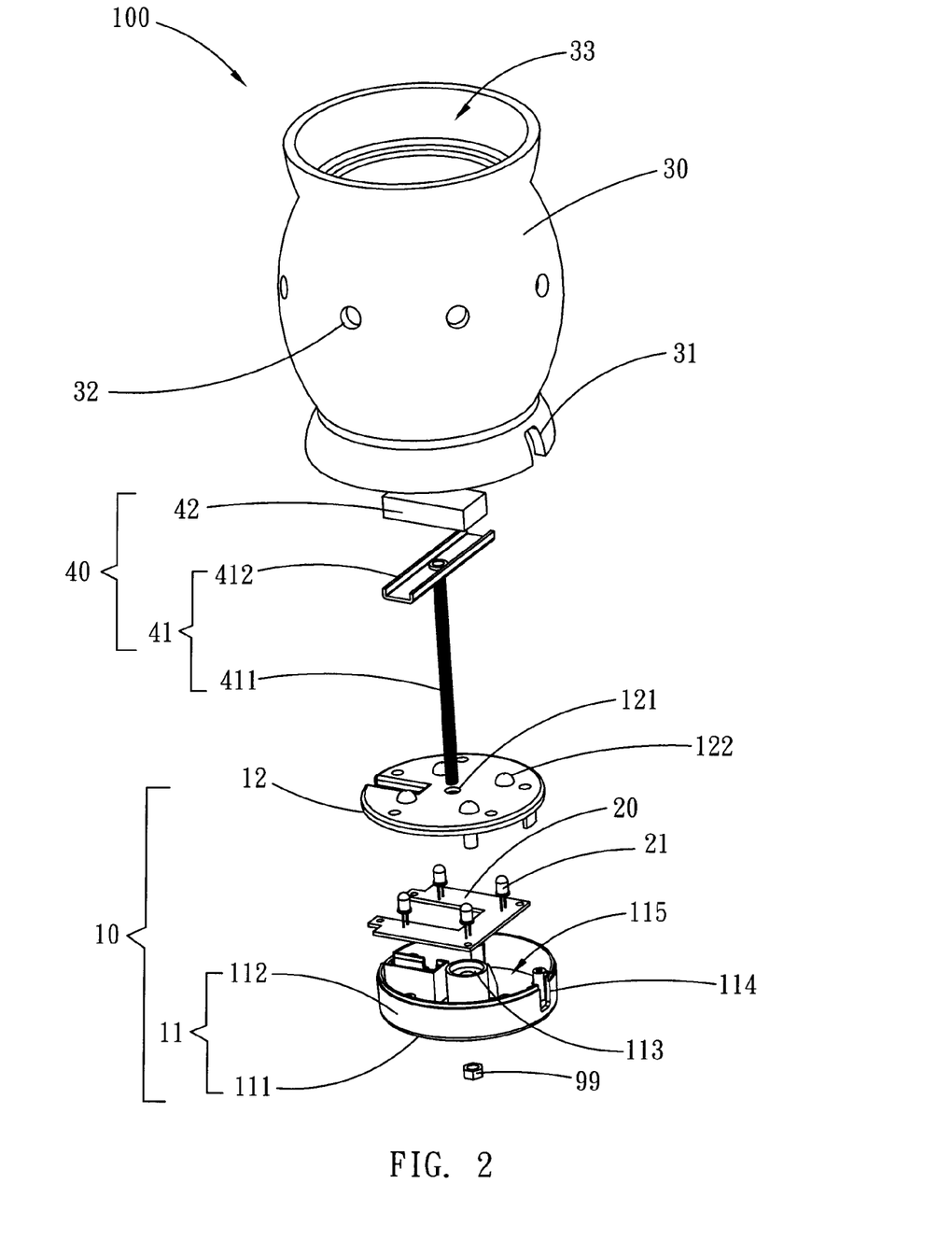
FIG. 2 is an exploded view showing the preferable embodiment of the present invention.
Figure 3:
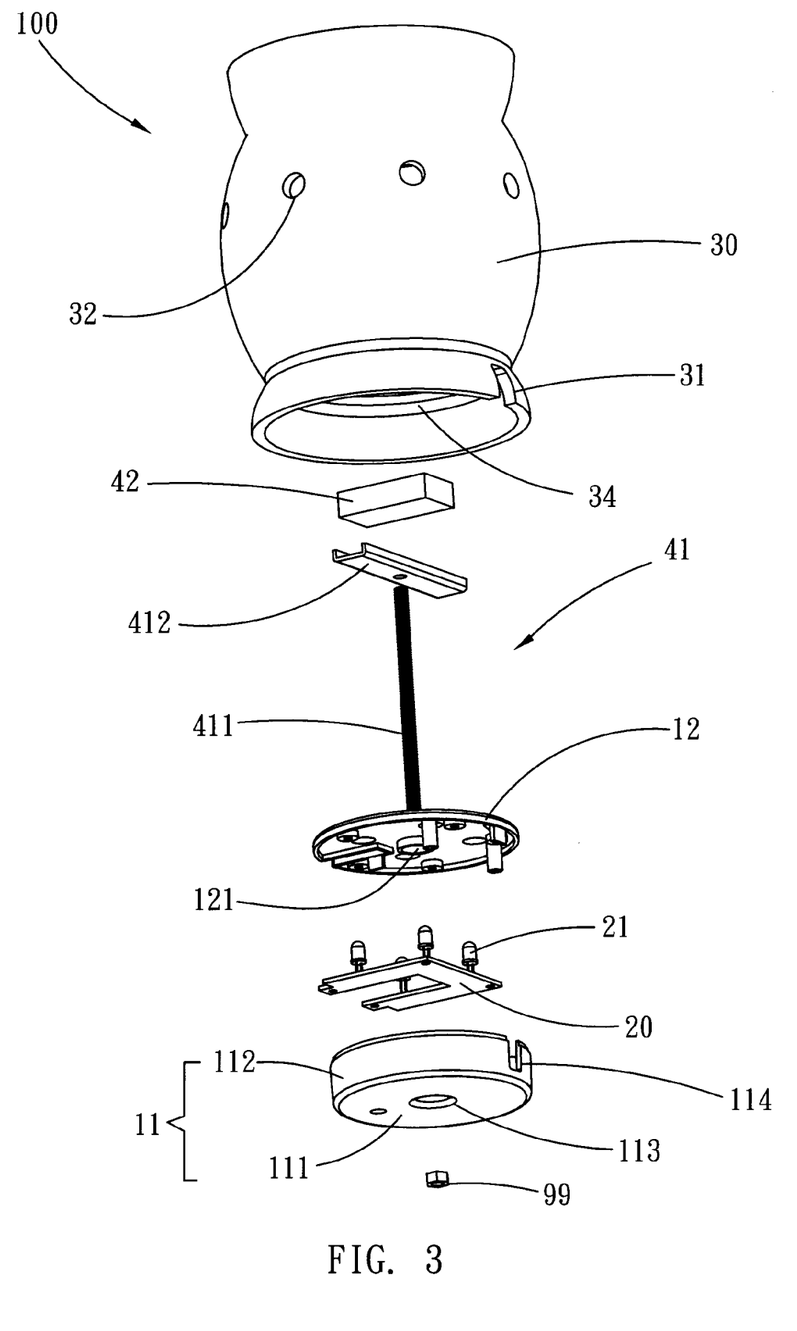
FIG. 3 is an exploded view showing the preferable embodiment of the present invention in other viewing angle.
Figure 4:
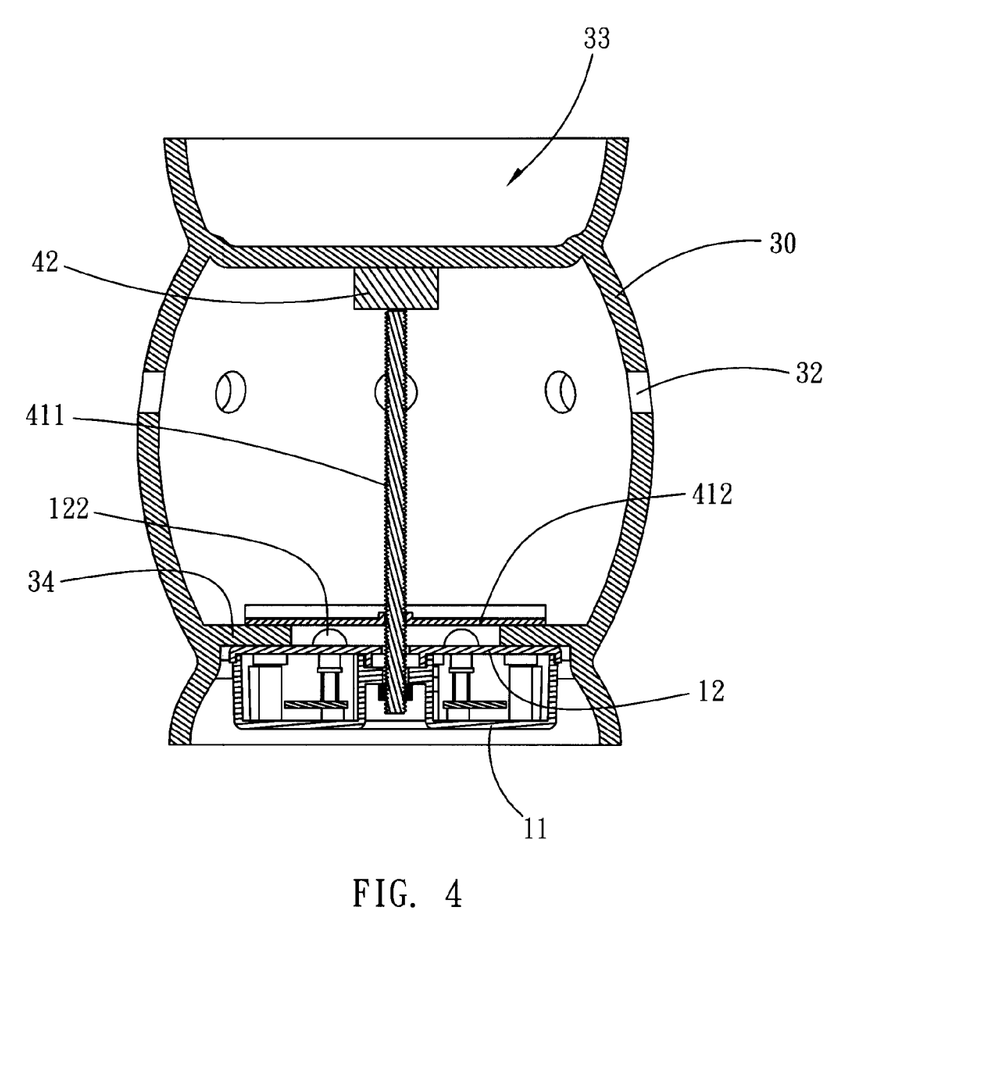
FIG. 4 is a cross section view showing the preferable embodiment of the present invention.

With reference to FIGS. 1 to 4, a preferable embodiment of a safe illuminating fragrant device 100 according to the present invention includes a base 10, an electrical circuit 20, a case body 30, and an electrothermal unit 40.

The base 10 has through hole 113 in a bottom thereof.

The electrical circuit 20 serves to connect to an external power source so as to supply power to the electrothermal unit 40. The electrical circuit 20 having a plurality of lighting component 21 is arranged inside the base 10.

The case body 30 is a whole body connecting to the base 10. A plurality of apertures 32 is arranged around a peripheral of the case body 30 with a predetermined interval. A receiving slot 33 on a top of the case body 30 is capable of receiving a spice such as essential oil or fragrant wax.

The electrothermal unit 40 includes a carrier 41 and a heater 42. An end of the carrier 41 is connected to the through hole 113. The heater 42 is connected to another end of the carrier 41 and contacts a bottom of the receiving slot 33. The heater 42 is electrified through the electric circuit 20 to be heated up so that the spice in the receiving slot 33 will be warmed up and release the fragrance.

The base 10 further includes a cut 114 for a power cord connecting to the external power source. The case body 30 also has a cut 31 in the bottom corresponding to the cut 114. The power cord will pass through the cut 114 and cut 31 to supply power to the electric circuit 20.

The carrier 41 of the electrothermal unit 40 has a screw 411. An end of the screw 411 passes through the through hole 113 and is screwed by a nut 99.

The base 10 further includes a bottom case 11 and a cover 12. The bottom case 11 has a plate 111 and a wall 112 extending from an edge of the plate 111. A receiving space 115 is defined by the plate 111 and the wall 112. The through hole 113 is formed to the plate 111. The cut 114 for power cord is formed to the wall 112. The cover 12 will cover upon the bottom case 11. A through hole 121 opposite to the through hole 113 of the base 10 is formed to the cover 12 for passing through by the screw 411 of the electrothermal unit 40.

A plurality of transparent shields is formed to the cover 12 corresponding to the plurality of the lighting components 21 of the electric circuit 20 so that light from the plurality of lighting units 20 will come into the case body 30. Lights will also come out from the apertures 32 of the case body 30 so as to perform an illumination feature. In the same time, the cover 12 can ensure that the essential oil will not leak to the lighting components and cause a safety issue if the case body is broken or tumbled.

The electric circuit 20 is arranged to the receiving space 115 in the base 10.

A lower flange 34 extending from an inner round surface is formed near the bottom of the case body 30. A top of the base 10 is pushed against a bottom of the flange 34. The electrothermal unit 40 has a retaining sheet 412 screwed to the screw 411. The retaining sheet 412 is cover upon the flange 34 so that the case body 30 can be clamped by the retaining sheet 412, base 10, screw 411, and the nut 99.

The present invention is easy to assemble and disassemble so that users can perform it by their own.

The heater 42 of the electrothermal unit 40 can be a mica heater, Positive Temperature Coefficient (PTC) thermistor, or cement resistor. Such heater has an insulated surface so that there is no safety issue like burning while the essential oil is leaking.

The case body 30 can be a transparent, or semi-transparent case body so that user can also enjoy shining of lights passing through.

The lighting component 21 of the electric circuit 20 can be a Light Emitting Diode (LED) such as a red, blue, green or any other color LED chip, or LEDs with different color.

Figure 5:
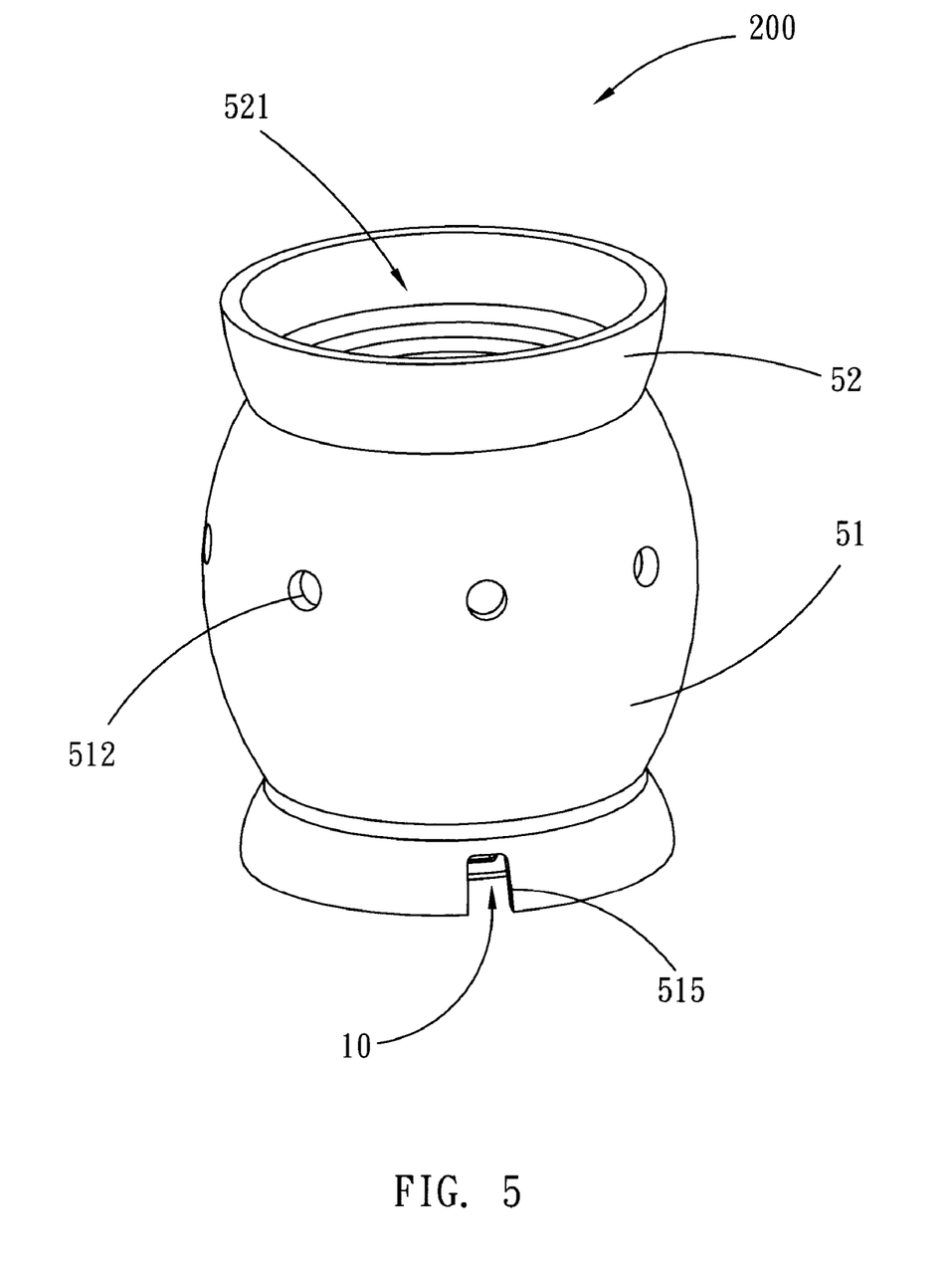
FIG. 5 is a schematic view showing a second embodiment of the present invention.
Figure 6:
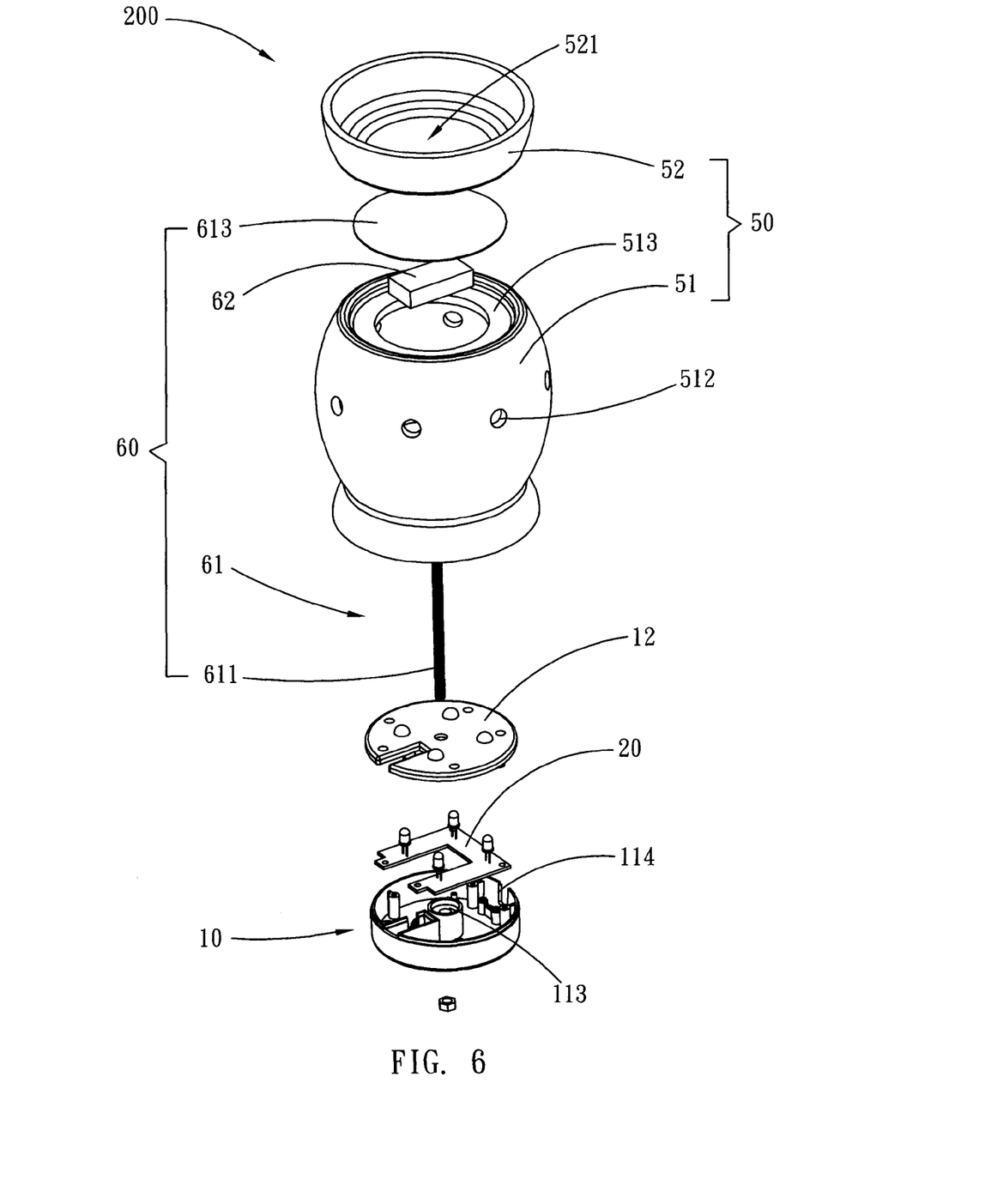
FIG. 6 is an exploded view showing the second embodiment of the present invention.
Figure 7:
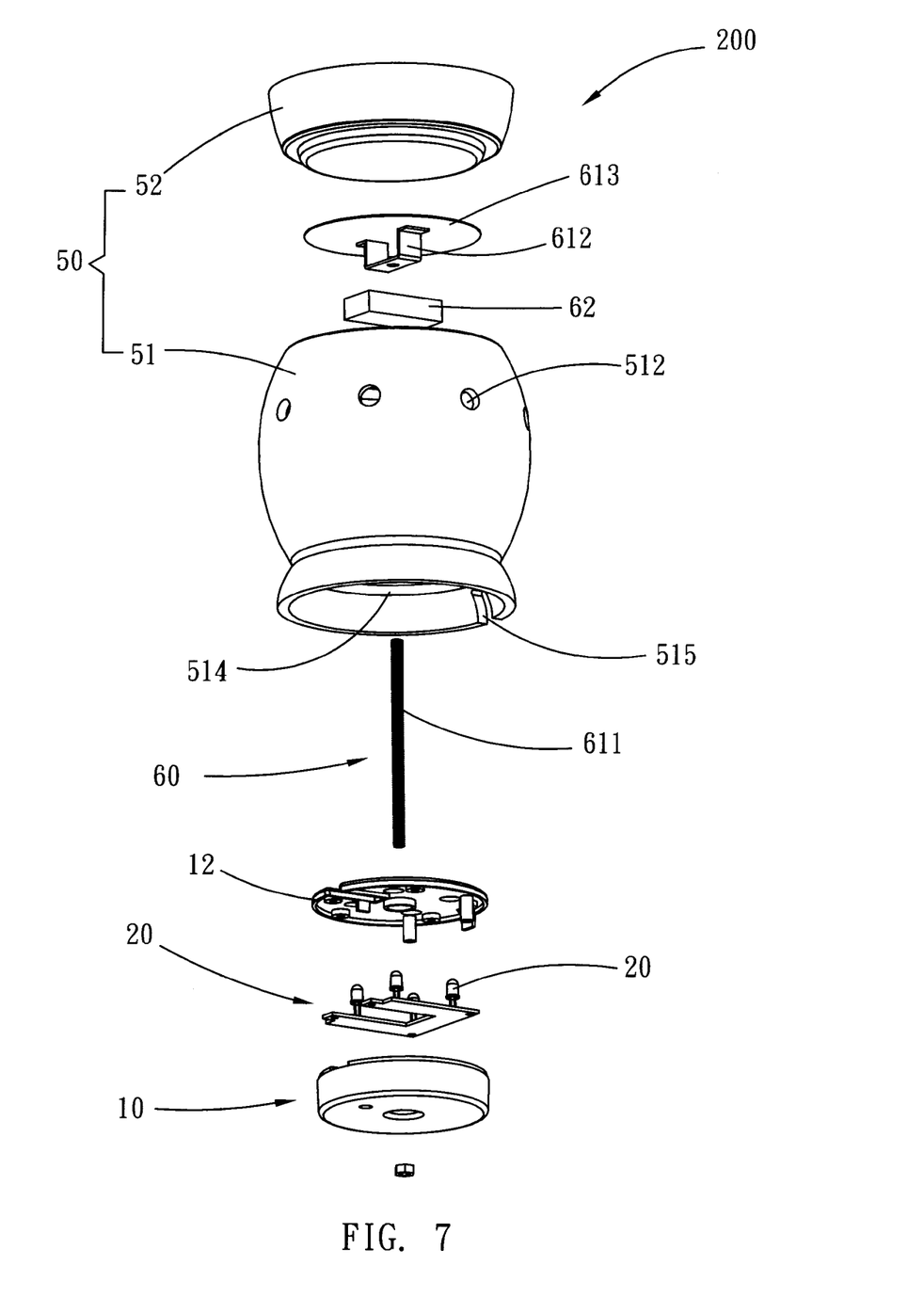
FIG. 7 is an exploded view showing the second embodiment of the present invention in other viewing angle.
Figure 8:
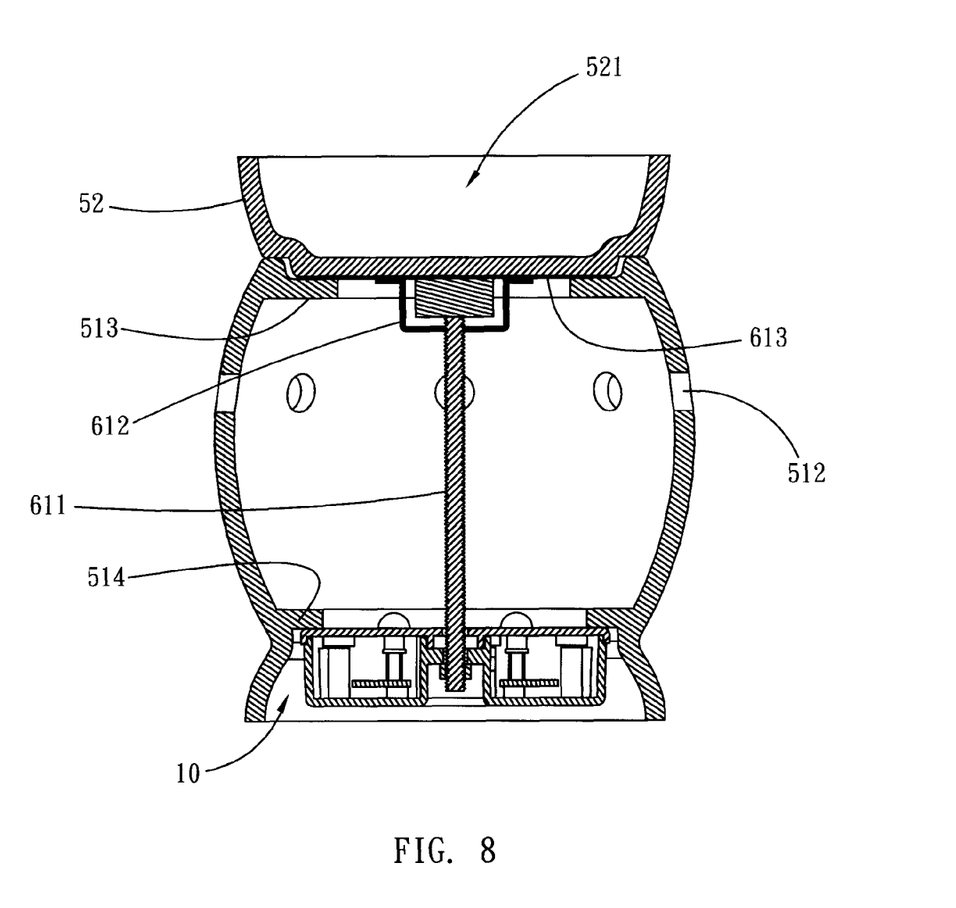
FIG. 8 is a cross section view showing the second embodiment of the present invention.

Referring to FIGS. 5 to 8, another embodiment of the present invention is shown. The safe illuminating fragrant device 200 also includes a base 10, an electric circuit 20, a case body 50, and an electrothermal unit 60.

The case body 50 has a hollow case 51 and a container 52. The hollow case 51 has a cut 515 in a bottom thereof. The hollow case 51 covers upon the base 10, and the cut 515 of the hollow case 51 is opposite to the cut 114 of the base 10. A plurality of apertures 512 is arranged around a peripheral of the hollow case 51 with a predetermined interval. The apertures 512 serve to illuminate while a lighting component 21 is operated and also to dissipate heat from the lighting component 21 and a heater 62 of the electrothermal unit 60. An upper flange 513 and a lower flange 514 extending from an inner peripheral are formed near a top and the bottom of the hollow case 51 respectively. The lower flange 514 is fixed to the base 10. The container 52 has a receiving slot 521 for receiving the spices, and a bottom of the container 52 contacts the upper flange 513 of the hollow case 51.

The electrothermal unit 60 has a carrier 61 and the heater 62. The carrier 61 has a screw 611, carrier seat 612, and a conducting sheet 613. The screw 611 is arranged inside the hollow case 51. An end of the screw 611 is connected to the through hole 113 of the base 10. The carrier seat 612 is connected to another end of the screw 611. The heater 62 is arranged to the carrier seat 612 of the carrier 61. The conducting sheet 613 seated on the carrier seat 612 is arranged upon the upper flange 513 of the hollow case 51 so as to conduct heat from the heater 62 to the spice in the container 52.

Through above components, the hollow case 51 and the container 52 are separable. The container 52 can be removed from the conducting sheet 613 so that user can conveniently perform a cleaning for a purpose of changing spice with different fragrance such as essential oil, wax or dried herb.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A safe illuminating fragrant device comprising:
   a base having a through hole;
   an electric circuit having a plurality of lighting components capable of emitting lights in predetermined color; the electric circuit being arranged inside the base;
   a case body having a lower flange in an inner peripheral for connecting the base; the base being covered by the case body; a plurality of apertures for revealing lights from the lighting component being arranged around a peripheral of the case body with a predetermined interval; a receiving slot being formed to a convex top of the case body for receiving a spice;
   a electrothermal unit having a carrier and a heater; an end of the carrier fixed to the through hole of the base; another end of the carrier connecting the heater; the heater touching a bottom of the receiving slot; the heater being supplied power through the electrical circuit for heating up.

2. The safe illuminating fragrant device as claimed in claim 1, wherein the base includes a bottom case and a cover; the bottom case has a plate and a wall extending from an edge of the plate; a receiving space is defined by the plate and the wall for receiving the electrical circuit; the cover is covered upon the bottom case.

3. The safe illuminating fragrant device as claimed in claim 2, wherein a plurality of transparent shields is formed to the cover corresponding to the plurality of the lighting component of the electric circuit.

4. The safe illuminating fragrant device as claimed in claim 1, wherein the base includes a cut for an external power cord; the electric circuit has a power connector; the case body has a cut opposite to the cut of the base; the power connector of the electric circuit will be connected with electricity power cord through the cuts for supplying power to the electric circuit.

5. The safe illuminating fragrant device as claimed in claim 1, wherein the electrothermal unit is one of a mica heater, Positive Temperature Coefficient (PTC) thermistor, or cement resistor.

6. The safe illuminating fragrant device as claimed in claim 1, wherein the case body is one of a transparent or semi-transparent body.

7. The safe illuminating fragrant device as claimed in claim 1, wherein the lighting component of the electric circuit is a Light Emitting Diode (LED) and is one of a red, blue, green LED chips, or at least one LED with multiple chips capable of emitting different color of light by mixing red, blue, and green lights.

8. The safe illuminating fragrant device as claimed in claim 1, wherein the case body has a hollow case and a container; an upper flange extending from the inner peripheral is formed near a top of the hollow case; the container has a receiving slot on a top thereof; a bottom of the container contacts the upper flange of the hollow case.

9. The safe illuminating fragrant device as claimed in claim 8, wherein the carrier has a screw, carrier seat, and a conducting sheet; an end of the screw is connected to the through hole of the base; the carrier seat is connected to another end of the screw; the conducting sheet seated on the carrier seat is arranged upon the upper flange of the hollow case so as to conduct heat from the heater to the container.

10. The safe illuminating fragrant device as claimed in claim 1, wherein the carrier of the electrothermal unit has a screw and a retaining sheet; an end of the screw passes through the through hole and is screwed by a nut; the retaining sheet is screwed to the screw and covers upon the lower flange so that the case body can be clamped by the retaining sheet, base, screw, and the nut.

\* \* \* \* \*